United States Patent
Paruch et al.

(10) Patent No.: US 7,074,795 B2
(45) Date of Patent: Jul. 11, 2006

(54) 17β-HYDROXYSTEROID DEHYDROGENASE TYPE 3 INHIBITORS FOR THE TREATMENT OF ANDROGEN DEPENDENT DISEASES

(75) Inventors: Kamil Paruch, Garwood, NJ (US); Timothy J. Guzi, Chatham, NJ (US)

(73) Assignee: Schering Corporation, Kenilworth, NJ (US)

( * ) Notice: Subject to any disclaimer, the term of this patent is extended or adjusted under 35 U.S.C. 154(b) by 288 days.

(21) Appl. No.: 10/713,828

(22) Filed: Nov. 14, 2003

(65) Prior Publication Data

US 2004/0127503 A1 Jul. 1, 2004

Related U.S. Application Data

(60) Provisional application No. 60/427,263, filed on Nov. 18, 2002.

(51) Int. Cl.
*A61K 31/496* (2006.01)
*C07D 401/12* (2006.01)

(52) U.S. Cl. .................. 514/253.01; 544/360; 546/188; 546/190; 514/316

(58) Field of Classification Search ................ 544/360; 514/253.01
See application file for complete search history.

(56) References Cited

FOREIGN PATENT DOCUMENTS

| | | |
|---|---|---|
| WO | WO 86/01105 | 2/1986 |
| WO | WO 90/10462 | 9/1990 |
| WO | WO 91/00731 | 1/1991 |
| WO | WO 91/00733 | 1/1991 |
| WO | WO 94/26767 | 11/1994 |
| WO | WO 96/26201 | 8/1996 |
| WO | WO 97/11162 | 3/1997 |
| WO | WO 99/46279 | 9/1999 |
| WO | WO 03/022835 | 3/2003 |
| WO | WO 03/033487 | 4/2003 |

OTHER PUBLICATIONS

R. Le Lain et al., "Some Coumarins and Triphenylethene Derivatives as Inhibitors of Human Testes Microsomal 17β-hydroxysteroid Dehydrogenase (17β-HSD Type 3): Further Studies with Tamoxifen on the Rat Testes Microsomal Enzyme", *J. Enzyme Inhibition and Medecinal Chemistry*, 17(2):93-100, (2002).

*Primary Examiner*—Emily Bernhardt
(74) *Attorney, Agent, or Firm*—Palaiyur S. Kalyanaraman

(57) ABSTRACT

In its many embodiments, the present invention provides a novel class of compounds as inhibitors of type 3 17 β-hydroxysteroid dehydrogenase, methods of preparing such compounds, pharmaceutical compositions containing one or more such compounds, methods of preparing pharmaceutical formulations comprising one or more such compounds, and methods of treatment, prevention, inhibition, or amelioration of one or more diseases associated with type 3 17 β-hydroxysteroid dehydrogenase using such compounds or pharmaceutical compositions. In one embodiment, the present invention discloses a compound having the general structure shown in Formula I:
wherein the various moieties are as defined herein.

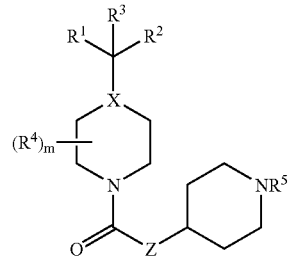

Formula I

21 Claims, No Drawings

17β-HYDROXYSTEROID DEHYDROGENASE TYPE 3 INHIBITORS FOR THE TREATMENT OF ANDROGEN DEPENDENT DISEASES

FIELD OF THE INVENTION

This invention relates to inhibitors of Type 3 17β-hydroxysteroid dehydrogenase, compositions containing the inhibitors, and methods of using the inhibitors for the treatment or prevention of androgen dependent diseases. This application claims priority from U.S. provisional patent application Ser. No. 60/427,263 filed Nov. 18, 2002.

BACKGROUND OF THE INVENTION

Androgen dependent diseases, for example, diseases whose onset or progress is aided by androgenic activity, are well known. These diseases include, but are not limited to, prostate cancer, benign prostatic hyperplasia, acne, seborrhea, hirsutism, androgenic alopecia, precocious puberty, adrenal hyperlasia and polycystic ovarian syndrome. Estrogen dependent diseases, for example, diseases whose onset or progress is aided by estrogenic activity, are also well known. These include, but are not limited to, breast cancer, endometriosis, leiomyoma and precocious puberty.

Androgenic and estrogenic activities can be suppressed by administering, respectively, androgen and estrogen receptor antagonists. See, for e.g., WO 94/26767 and WO 96/26201. Androgenic and estrogenic activities can also be reduced by suppressing androgen and estrogen biosyntheses using inhibitors of enzymes that catalyze one or more steps of such biosyntheses. 17β-HSD3 is the primary enzyme that converts androstenedione to testosterone in the testes. Inhibitors of both Type 3 and Type 5 17β-hydroxysteroid dehydrogenase are described in WO 99/46279. Inhibitors of Type 5 17β-hydroxysteroid dehydrogenase is also described in WO 97/11162. Androgenic and estrogenic activities can also be reduced by suppressing ovarian or testicular secretions by known methods. See, for e.g., WO 90/10462, WO 91/00731, WO 91/00733 and WO 86/01105.

Commonly owned, pending U.S. patent applications, Ser. No. 10/235,627, filed Sep. 5, 2002, and Ser. No. 10/271,358, filed Oct. 15, 2002, disclose certain types of inhibitors of type 3 17β-hydroxysteroid dehydrogenase. There is a continuing need for new compounds, formulations, treatments and therapies to treat diseases and disorders associated with type 3 17β-hydroxysteroid dehydrogenase. It is, therefore, an object of this invention to provide compounds useful in the treatment or prevention or amelioration of such diseases and disorders.

SUMMARY OF THE INVENTION

In its many embodiments, the present invention provides a novel class of compounds as inhibitors of type 3 17β-hydroxysteroid dehydrogenase, methods of preparing such compounds, pharmaceutical compositions comprising one or more such compounds, methods of preparing pharmaceutical compositions comprising one or more such compounds, and methods of treatment, prevention, inhibition or amelioration of one or more diseases associated with type 3 17β-hydroxysteroid dehydrogenase using such compounds or pharmaceutical compositions.

In one aspect, the present application discloses a compound, or a pharmaceutically acceptable salt or solvate of said compound, said compound having the general structure shown in Formula I:

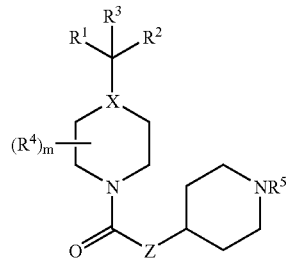

Formula I wherein:

X is CH or N;

Z is O or $N(R^6)$;

$R^1$ and $R^2$ are the same or different, each being independently selected from the group consisting of aryl, heteroaryl, aralkyl and heteroaralkyl, wherein each of said aryl, heteroaryl, aralkyl and heteroaralkyl can be unsubstituted or optionally independently substituted with one or more moieties which can be the same or different, each moiety being independently selected from the group consisting of halogen, alkyl, aryl, heteroaryl, aralkyl, heteroaralkyl, cycloalkyl, heterocyclyl, $CF_3$, CN, —$OCF_3$, —$OR^6$, —C(O)$R^7$, —$NR^6R^7$, —C(O)$OR^6$, —C(O)$NR^6R^7$, —$SR^6$, —$S(O_2)R^7$, —$S(O_2)NR^6R^7$, —$N(R^6)S(O_2)R^7$, —$N(R^6)C(O)R^7$ and —$N(R^6)C(O)NR^6R^7$;

$R^3$ is H or —$OR^6$, with the proviso that when X is N, $R^3$ is not —$OR^6$;

$R^4$ is selected from the group consisting of H, alkyl, aryl, cycloalkyl, aralkyl, heteroaryl, heteroaralkyl and heterocyclyl;

m is a number from 0 to 4, and when m is more than 1, the $R^4$ groups can be the same or different and are independently selected;

$R^5$ is —C(O)$R^7$ or —$S(O_2)R^7$;

$R^6$ is selected from the group consisting of H, alkyl, aryl, heteroaryl, aralkyl, heteroaralkyl, cycloalkyl and heterocyclyl, wherein each of said alkyl, aryl, heteroaryl, aralkyl, heteroaralkyl, cycloalkyl and heterocyclyl can be unsubstituted or optionally independently substituted with one or more moieties which can be the same or different, each moiety being independently selected from the group consisting of halogen, alkyl, aryl, cycloalkyl, $CF_3$, $OCF_3$, CN, —$OR^7$, —$NHR^7$, —$N(R^7)_2$, —$CH_2OR^7$, —C(O)$R^7$, —C(O)$OR^7$, —C(O)$NHR^7$, —C(O)$N(R^7)_2$, —$SR^7$, —$S(O_2)R^7$, —$S(O_2)NHR^7$, —$S(O_2)N(R^7)_2$, —$N(R^7)S(O_2)R^7$, —$N(R^7)C(O)R^7$, —$N(R^7)C(O)NHR^7$ and —$N(R^7)C(O)N(R^7)_2$; and $R^7$ is selected from the group consisting of alkyl, aryl, heteroaryl, aralkyl, heteroaralkyl, —$OR^6$, —$NHR^6$, and —$N(R^6)_2$, wherein each of said alkyl, heteroaralkyl, aryl, heteroaryl and aralkyl can be unsubstituted or optionally substituted with one or more moieties which can be the same or different, each moiety being independently selected from the group consisting of halogen, alkyl, aryl, cycloalkyl, $CF_3$, $OCF_3$, CN, —$OR^6$, —$NHR^6$, —$N(R^6)_2$, —$CH_2OR^6$, —C(O)$OR^6$, —C(O)$NHR^6$, —C(O)$N(R^6)_2$, —$SR^6$, —$S(O_2)R^6$, —$S(O_2)NHR^6$, —$S(O_2)N(R^6)_2$, —$N(R^6)S(O_2)R^6$, —$N(R^6)C(O)R^6$, —$N(R^7)C(O)NHR^6$ and —$N(R^7)C(O)

$N(R^7)_2$, further wherein the two $R^6$ or the two $R^7$ groups in the moieties —$N(R^6)_2$ and —$N(R^7)_2$ respectively can be the same or different and are independently selected, and still further wherein any two adjacent alkyl substituents on an aryl or heteroaryl can be joined together to form a methylenedioxy or ethylenedioxygroup.

The compounds of Formula I can be useful as inhibitors of type 3 17β-hydroxysteroid dehydrogenase and can be useful in the treatment and prevention of diseases associated with type 3 17β-hydroxysteroid dehydrogenase.

DETAILED DESCRIPTION

In one embodiment, the present invention discloses compounds which are represented by structural Formula I, or a pharmaceutically acceptable salt or solvate thereof, wherein the various moieties are as described above.

In a preferred embodiment, X is CH.
In another preferred embodiment, X is N.
In another preferred embodiment, Z is $N(R^6)$.
In another preferred embodiment, $R^1$ and $R^2$ are the same and are aryl or heteroaryl, wherein each of said aryl and heteroaryl is either unsubstituted or optionally independently substituted with one or more moieties which can be the same or different, each moiety being independently selected from the group consisting of halogen, alkyl, —$CF_3$, —CN, —$OCF_3$, —$OR^6$, —$C(O)R^7$, and —$C(O)OR^6$.

In another preferred embodiment, $R^3$ is H.
In another preferred embodiment, m is 1–2.
In another preferred embodiment, $R^4$ is H or alkyl.
In another preferred embodiment, $R^5$ is —$C(O)R^7$.
In another preferred embodiment, $R^5$ is —$S(O_2)R^7$.
In another preferred embodiment, $R^6$ is selected from the group consisting of H, alkyl, aryl, —$CF_3$, —$C(O)R^7$ and —$S(O_2)R^7$.
In another preferred embodiment, $R^7$ is selected from the group consisting of alkyl, aralkyl and aryl.
In an additional preferred embodiment, Z is NH.
In an additional preferred embodiment, $R^1$ and $R^2$ are the same and are both phenyl, which are either unsubstituted or optionally independently substituted with one or more moieties which can be the same or different, each moiety being independently selected from the group consisting of Cl, Br, methyl, tert-butyl, —$CF_3$, and —$OCF_3$.
In an additional preferred embodiment, m is 1.
In an additional preferred embodiment, $R^4$ is H.
In an additional preferred embodiment, $R^4$ is alkyl.
In an additional preferred embodiment, $R^5$ is —$C(O)CH_3$.
In an additional preferred embodiment, $R^6$ is H, methyl, phenyl, —$C(O)CH_3$ or —$S(O_2)CH_3$.
In an additional preferred embodiment, $R^7$ is methyl.

A particularly preferred group of compounds are shown in Table 1, including all their isomers, racemates and the like.

TABLE 1

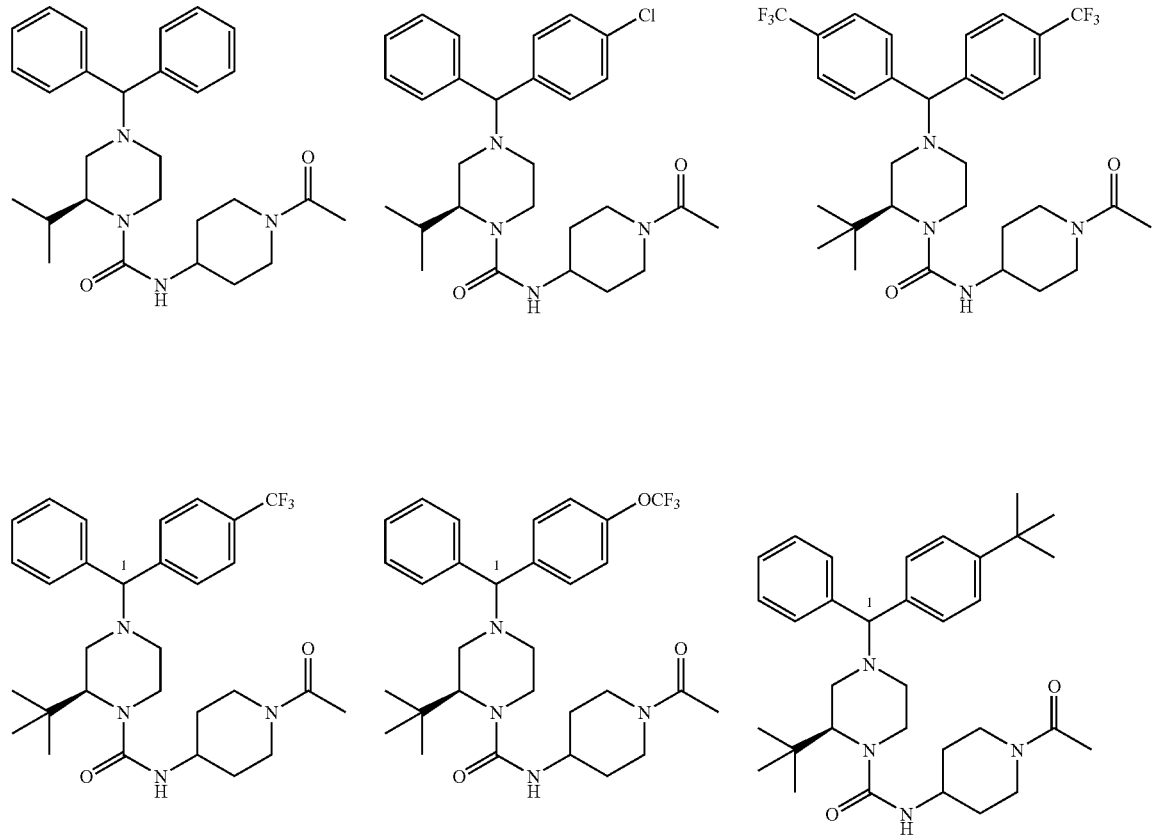

TABLE 1-continued

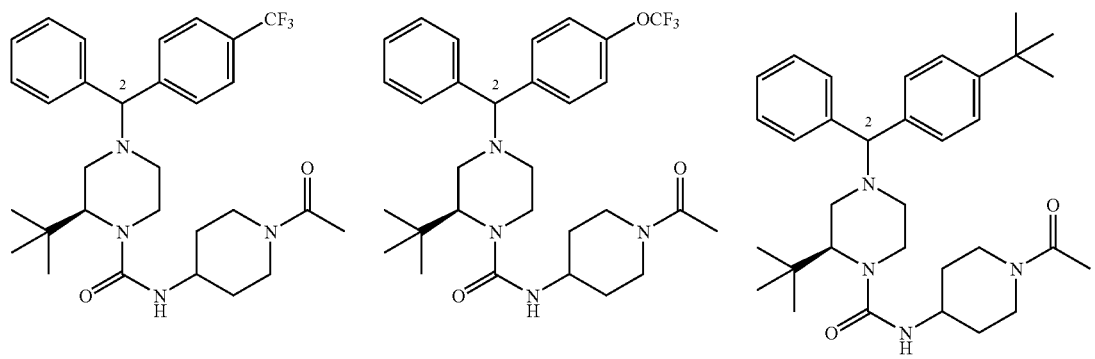

The numbers on the bridge atom in the structures above indicate diastereomers.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched.

"Aryl" means an aromatic monocyclic or multicyclic ring system comprising about 6 to about 14 carbon atoms, preferably about 6 to about 10 carbon atoms. Non-limiting examples of suitable aryl groups include phenyl and naphthyl.

"Heteroaryl" means an aromatic monocyclic or multiclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, N-oxide of pyridyl, pyrazinyl, furanyl (furyl), thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,5-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Halogen" or "halo" means fluorine, chlorine, bromine, or iodine.

"Heterocyclyl" (or heterocycloalkyl) means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Ring system substituent" means a substituent attached to an aromatic or non-aromatic ring system which, for example, replaces an available hydrogen on the ring system. Ring system substituents may be the same or different, each being independently selected from the group consisting of alkyl, aryl, heteroaryl, aralkyl, alkylaryl, aralkenyl, heteroaralkyl, alkylheteroaryl, heteroaralkenyl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylsulfinyl, arylsulfinyl, heteroarylsulfinyl, alkylthio, arylthio, heteroarylthio, aralkylthio, heteroaralkylthio, cycloalkyl, cycloalkenyl, heterocyclyl, heterocyclenyl, $Y_1Y_2N-$, $Y_1Y_2N$-alkyl-, $Y_1Y_2NC(O)-$ and $Y_1Y_2NSO_2-$, wherein $Y_1$ and $Y_2$ may be the same or different and are independently selected from the group consisting of hydrogen, alkyl, aryl, and aralkyl. "Ring system substituent" also means a cyclic ring of 3 to 7 ring atoms of which 1–2 may be a heteroatom, attached to an aryl, heteroaryl, heterocyclyl or heterocyclenyl ring by simultaneously substituting two ring hydrogen atoms on said aryl, heteroaryl, heterocyclyl or heterocyclenyl ring. Non-limiting examples include:

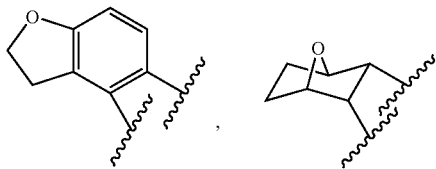

and the like.

The term "heteroaralkyl" or "heteroarylalkyl" means a heteroaryl-alkyl-group in which the heteroaryl and alkyl are as previously described. Preferred heteroarylalkyls comprise a lower alkyl group. Non-limiting examples of suitable heteroarylalkyl groups include pyridin-4-ylmethyl, thien-3-ylmethyl and the like. The bond to the parent moiety is through the alkyl.

The term "heterocyclylalkyl" means a heterocyclyl-alkyl-group in which the heterocyclyl and alkyl are as previously described. Preferred heterocyclylalkyls comprise a lower alkyl group. Non-limiting examples of suitable heterocyclylalkyl groups include piperidin-4-ylmethyl, pyrrolidin-3-ylmethyl and the like. The bond to the parent moiety is through the alkyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

It should also be noted that any carbon or heteroatom with unsatisfied valences in the text, schemes, examples, structural formulae, and Tables herein is assumed to have the hydrogen atom or atoms to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York. When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of Formula III or a salt and/or solvate thereof. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the type 3 17β-hydroxysteroid dehydrogenase and thus producing the desired therapeutic, ameliorative, inhibitory or preventative effect.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection*, and *Use*, (2002) Int'l. Union of Pure and Applied Chemistry, pp. 330–331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like.

Exemplary basic salts include ammonium salts, alkali metal salts such as sodium, lithium, and potassium salts, alkaline earth metal salts such as calcium and magnesium salts, aluminum. salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate" "prodrug" and the like, is intended to equally apply to the salt, solvate and prodrug of enantiomers, stereoisomers, rotamers, tautomers, positional isomers, racemates or prodrugs of the inventive compounds.

The invention also includes the inventive compounds in isolated and purified form.

The compounds according to the invention have pharmacological properties; in particular, the compounds of Formula I can be inhibitors of type 3 17β-hydroxysteroid dehydrogenase. The novel compounds of Formula I are expected to be useful in the therapy of proliferative diseases associated with type 3 17β-hydroxysteroid dehydrogenase.

More specifically, the compounds of Formula I can be useful in the treatment or prevention of androgen or estrogen dependent diseases in a patient in need thereof, which comprises administering to said patient a therapeutically effective amount of at least one compound of formula I.

In another aspect, the invention provides a method of treating or preventing prostate cancer, and other androgen-dependent neoplasms, benign prostatic hyperplasia, prostatic intraepithelial neoplasia, androgenic alopecia (i.e. pattern baldness in both male and female patients), hirsutism, polycystic ovary syndrome and acne in a patient in need thereof, which comprises administering to said patient, a therapeutically effective amount of at least one compound of formula I.

In another aspect, the invention provides a method of treating or preventing androgen-dependent diseases in a patient in need thereof, comprising administering (concurrently or sequentially) to said patient an effective amount of at least one compound of formula I in combination or association with at least one anti-androgenic agent (i.e. agents that decrease androgen synthesis or activity).

This invention also provides a method of treating or preventing benign prostatic hyperplasia in a patient in need thereof, comprising administering (concurrently or sequentially) to said patient an effective amount of at least one compound of formula I in combination or association with at least one agent useful in the treatment or prevention of benign prostatic hyperplasia.

This invention also provides a method of treating or preventing hair loss in a patient in need thereof, comprising administering (concurrently or sequentially) to said patient an effective amount of at least one compound of formula I in combination or association with at least one agent useful in the treatment or prevention of alopecia, e.g., potassium channel agonists or 5α-reductase inhibitors.

This invention also provides a method of treating or preventing hair loss, comprising administering (concurrently or sequentially) to a patient in need thereof, an effective amount of a compound of formula I in combination with at least one potassium channel agonist e.g. minoxidil and KC-516, or 5α-reductase inhibitor, e.g., finasteride.

The invention also provides a method of treating or preventing proliferative diseases in a patient in need thereof, especially cancers (tumors), comprising administering (concurrently or sequentially) to said patient an effective amount of (1) at least one compound of formula I in combination or association with (2) an effective amount of at least one anti-cancer agent i.e., a chemotherapeutic agent, biological agent, and/or surgery, e.g., prostatectomy and/or radiation therapy. Non-limiting examples of cancers (i.e. tumors) which may be inhibited or treated include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), renal cancers, myeloid leukemias (for example, acute myelogenous leukemia (AML), thyroid follicular cancer, myelodysplastic syndrome (MDS), bladder carcinoma, epidermal carcinoma, melanoma, breast cancer and prostate cancer.

The method of treating proliferative diseases (cancer), according to this invention, includes a method for treating (inhibiting) the abnormal growth of cells, including transformed cells, in a patient in need of such treatment, by administering, concurrently or sequentially, an effective amount of at least one compound of this invention and an effective amount of at least one chemotherapeutic agent, biological agent, surgery (e.g. prostatectomy) and/or radiation. Abnormal growth of cells means, for example, cell growth independent of normal regulatory mechanisms (e.g., contact inhibition or apoptosis), including the abnormal growth of: (1) tumor cells (tumors) expressing an activated ras oncogene; (2) tumor cells in which the ras protein is activated as a result of oncogenic mutation in another gene; and (3) benign and malignant cells of other proliferative diseases.

In its embodiments, the present invention includes methods for treating or inhibiting tumor growth in a patient in need of such treatment, by administering, concurrently or sequentially, (1) an effective amount of at least one compound of this invention and (2) an effective amount of at least one antineoplastic/microtubule agent, biological agent, and/or surgery (e.g. prostatectomy) and/or radiation therapy. Examples of tumors which may be treated include, but are not limited to, epithelial cancers, e.g., prostate cancer, lung cancer (e.g., lung adenocarcinoma), pancreatic cancers (e.g., pancreatic carcinoma such as, for example, exocrine pancreatic carcinoma), breast cancers, renal cancers, colon cancers (e.g., colorectal carcinomas, such as, for example, colon adenocarcinoma and colon adenoma), ovarian cancer, and bladder carcinoma. Other cancers that can be treated include melanoma, myeloid leukemias (for example, acute myelogenous leukemia), sarcomas, thyroid follicular cancer, and myelodysplastic syndrome.

As used herein the following terms have the following meanings unless indicated otherwise:

"Antineoplastic agent" means a chemotherapeutic agent effective against cancer;

"Concurrently" means (1) simultaneously in time, or (2) at different times during the course of a common treatment schedule; and "Sequentially" means (1) administration of one component of the method ((a) compound of the invention, or (b) antineoplastic agent and/or radiation therapy) followed by administration of the other component; after administration of one component, the second component can be administered substantially immediately after the first component, or the second component can be administered after an effective time period after the administration of the first component; the effective time period is the amount of time given for realization of maximum benefit from the administration of the first component.

A preferred dosage is about 0.001 to 500 mg/kg of body weight/day of the compound of Formula I. An especially preferred dosage is about 0.01 to 25 mg/kg of body weight/day of a compound of Formula I, or a pharmaceutically acceptable salt or solvate of said compound.

Certain useful combination/association agents are described below:

Chemotherapeutic Agents

Classes of compounds that can be used as the chemotherapeutic agent (antineoplastic agent) include: alkylating agents, antimetabolites, natural products and their derivatives, hormones and steroids (including synthetic analogs), and synthetics. Non-limiting examples of compounds within these classes are:

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylenemelamine, Triethylenethiophosphoramine, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), Mithramycin, Deoxycoformycin, Mitomycin-C, L-Asparaginase, Interferons-α and β (especially IFN-α), Etoposide, and Teniposide.

Hormonal agents and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin and Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, Navelbene, CPT-11, Anastrazole, Letrazole, Capecitabine, Ralozifine, Droloxifine and Hexamethylmelamine.

Non-limiting examples of biological agents useful in the methods of this invention include but are not limited to, interferon-α, interferon-β and gene therapy.

Microtubule Affecting Agents

As used herein, a microtubule affecting agent is a compound that interferes with cellular mitosis, i.e., having an anti-mitotic effect, by affecting microtubule formation and/or action. Such agents can be, for instance, microtubule stabilizing agents or agents which disrupt microtubule formation.

Non-limiting examples of microtubule affecting agents useful in the invention include allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), Taxol® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, discodermolide, estramustine, nocodazole, MAP4, and the like.

Particularly preferred agents are compounds with paclitaxel-like activity. These include, but are not limited to, paclitaxel and paclitaxel derivatives (paclitaxel-like compounds) and analogues. Paclitaxel and its derivatives are available commercially. More specifically, the term "paclitaxel" as used herein refers to the drug commercially available as Taxol®.

Examples of such agents include, but are not limited to, inhibitors of 5α-reductase type 1 and/or type 2, e.g. finasteride, SKF105,657, LY191,704, LY320,236, dutasteride, flutamide, nicalutamide, bicalutamide, LHRH agonists e.g. leuprolide and zoladex, LHRH antagonists, e.g. abarelix and cetrorelix, inhibitors of 17α-hydroxylase/C17–20 lyase, e.g. YM116, CB7630 and liarozole; inhibitors of 17β-hydroxysteroid dehydrogenase type 5 and/or other 17β-hydroxysteroid dehydrogenase/17β-oxidoreductase isoenzymes, e.g. EM-1404.

Types of androgen or estrogen dependent diseases include, but are not limited to, prostate cancer, benign prostatic hyperplasia, prostatic intraepithelial neoplasia, acne, seborrheas, hirsutism, androgenic alopecia, precocious puberty, adrenal hyperplasia, and polycystic ovarian syndrome, breast cancer, endometriosis and leiomyoma.

Examples of agents useful in the treatment or prevention of benign prostatic hyperplasia include, but are not limited to, α-1 adrenergic antagonists, e.g. tamsulosin and terazosin.

The pharmacological properties of the compounds of this invention may be confirmed by a number of pharmacological assays. The exemplified pharmacological assays which are described later have been carried out with the compounds according to the invention and their salts.

This invention is also directed to pharmaceutical compositions which comprise at least one compound of Formula I, or a pharmaceutically acceptable salt or solvate of said compound and at least one pharmaceutically acceptable carrier.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

The chemotherapeutic agent and/or radiation therapy can be administered in combination or association with the compounds of the present invention according to the dosage and administration schedule listed in the product information sheet of the approved agents, in the *Physicians Desk Reference* (PDR) as well as therapeutic protocols well known in the art. Table 2 below gives ranges of dosage and dosage regimens of some exemplary chemotherapeutic agents useful in the methods of the present invention. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered chemotherapeutic agents (i.e., antineoplastic agent or radiation) on the patient, and in view of the observed responses of the disease to the administered therapeutic agents.

TABLE 2

Exemplary Chemotherapeutic Agents
Dosage and Dosage Regimens

| | |
|---|---|
| Cisplatin: | 50–100 mg/m$^2$ every 4 weeks (IV)* |
| Carboplatin: | 300–360 mg/m$^2$ every 4 weeks (IV) |
| Taxotere: | 60–100 mg/m$^2$ every 3 weeks (IV) |
| Gemcitabine: | 750–1350 mg/m2 every 3 weeks (IV) |
| Taxol: | 65–175 mg/m2 every 3 weeks (IV) |

*(IV)-intravenously

Anti-androgenic agents, anti-benign prostatic hyperplasia agents, potassium channel agonists and biological agents can be administered in association with the compounds of the present invention according to the dosage and administration schedule listed in the product information sheet of the approved agents, in the *Physicians Desk Reference* (PDR) as well as therapeutic protocols well known in the art. It will be apparent to those skilled in the art that the administration of the agents can be varied depending on the disease being treated and the known effects of the agents on that disease. Also, in accordance with the knowledge of the skilled clinician, the therapeutic protocols (e.g., dosage amounts and times of administration) can be varied in view of the observed effects of the administered agents on the patient, and in view of the observed responses of the disease to the administered therapeutic agents.

Another aspect of this invention is a kit comprising a therapeutically effective amount of at least one compound of Formula I, or a pharmaceutically acceptable salt or solvate of said compound and a pharmaceutically acceptable carrier, vehicle or diluent.

Yet another aspect of this invention is a kit comprising an amount of at least one compound of Formula I, or a pharmaceutically acceptable salt or solvate of said compound and an amount of at least one additional agent listed above, wherein the amounts of the two or more ingredients result in desired therapeutic effect.

The above-described kits may contain the said ingredients in one or more containers within said kit.

The invention disclosed herein is exemplified by the following preparations and examples which should not be construed to limit the scope of the disclosure. Alternative mechanistic pathways and analogous structures will be apparent to those skilled in the art.

Where NMR data are presented, $^1$H spectra were obtained on either a Varian VXR-200 (200 MHz, $^1$H), Varian Gemini-300 (300 MHz) or XL-400 (400 MHz) and are reported as ppm down field from $Me_4Si$ with number of protons, multiplicities, and coupling constants in Hertz indicated parenthetically. Where LC/MS data are presented, analyses was performed using an Applied Biosystems API-100 mass spectrometer and Shimadzu SCL-10A LC column: Altech platinum C18, 3 micron, 33 mm x7 mm ID; gradient flow: 0 min—10% $CH_3CN$, 5 min—95% $CH_3CN$, 7 min—95% $CH_3CN$, 7.5 min—10% $CH_3CN$, 9 min—stop. The retention time and observed parent ion are given.

The following solvents and reagents may be referred to by their abbreviations in parenthesis:
Thin layer chromatography: TLC
ethyl acetate: AcOEt or EtOAc
methanol: MeOH
trifluoroacetate: TFA
triethylamine: TEA
butoxycarbonyl: n-Boc or Boc
nuclear magnetic resonance spectroscopy: NMR
liquid chromatography mass spectrometry: LCMS
high resolution mass spectrometry: HRMS
milliliters: mL
millimoles: mmol
microliters: µl
grams: g
milligrams: mg
room temperature or rt (ambient): about 25° C.

EXAMPLES

Compounds of formula (I) may be produced by processes known to those skilled in the art. Illustrative procedures are shown in the representative Schemes and Examples below.

These preparations and examples should not be construed to limit the scope of the disclosure. Alternative mechanistic pathways and analogous structures may be apparent to those skilled in the art. Some of the compounds made by these processes are listed in Table 1. As stated earlier, all kinds of isomeric forms of the compounds are considered to be within the scope of this invention.

Scheme 1

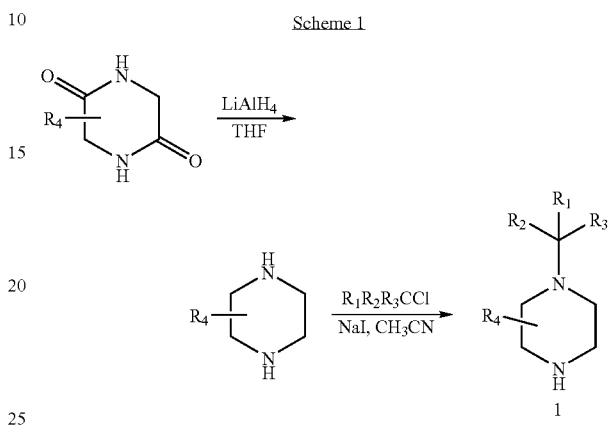

Reduction of 3-alkyl-2,5-piperazinediones afforded the corresponding piperazines. These were regioselectively alkylated to give compound 1. The benzylic chlorides were prepared as shown below.

The intermediates 2 and 3 are prepared from commercially available precursors as shown below.

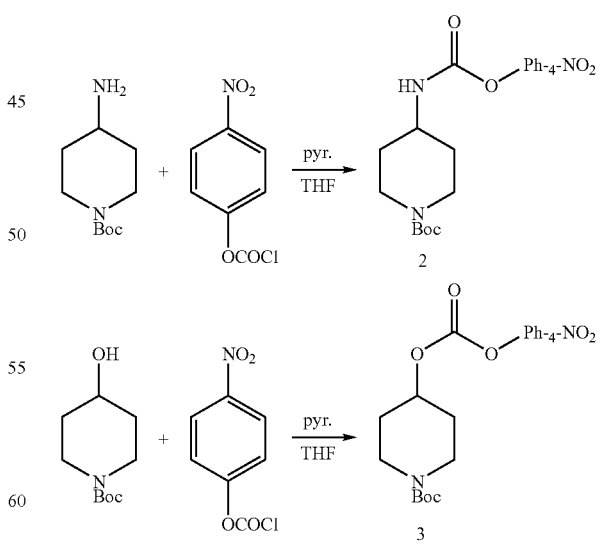

Piperazines 1, when combined with carbamate 2 afford ureas 4. Similarly, when the piperazines are combined with carbonate 3, afford carbamates 5. Boc-deprotection followed by acetylation provide the final products.

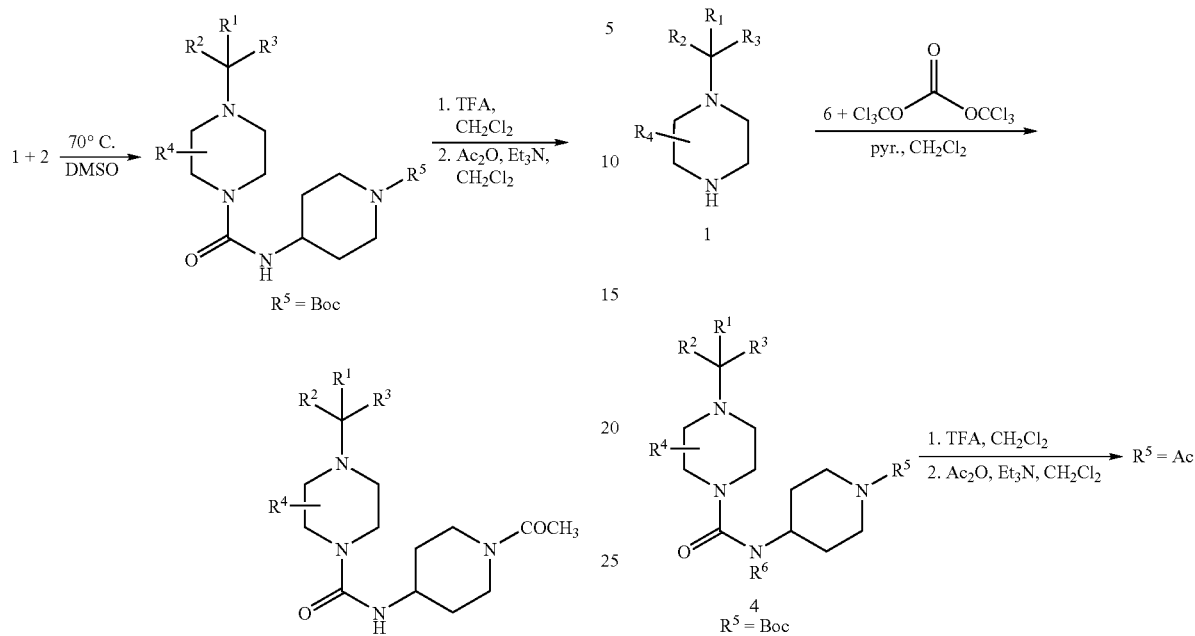
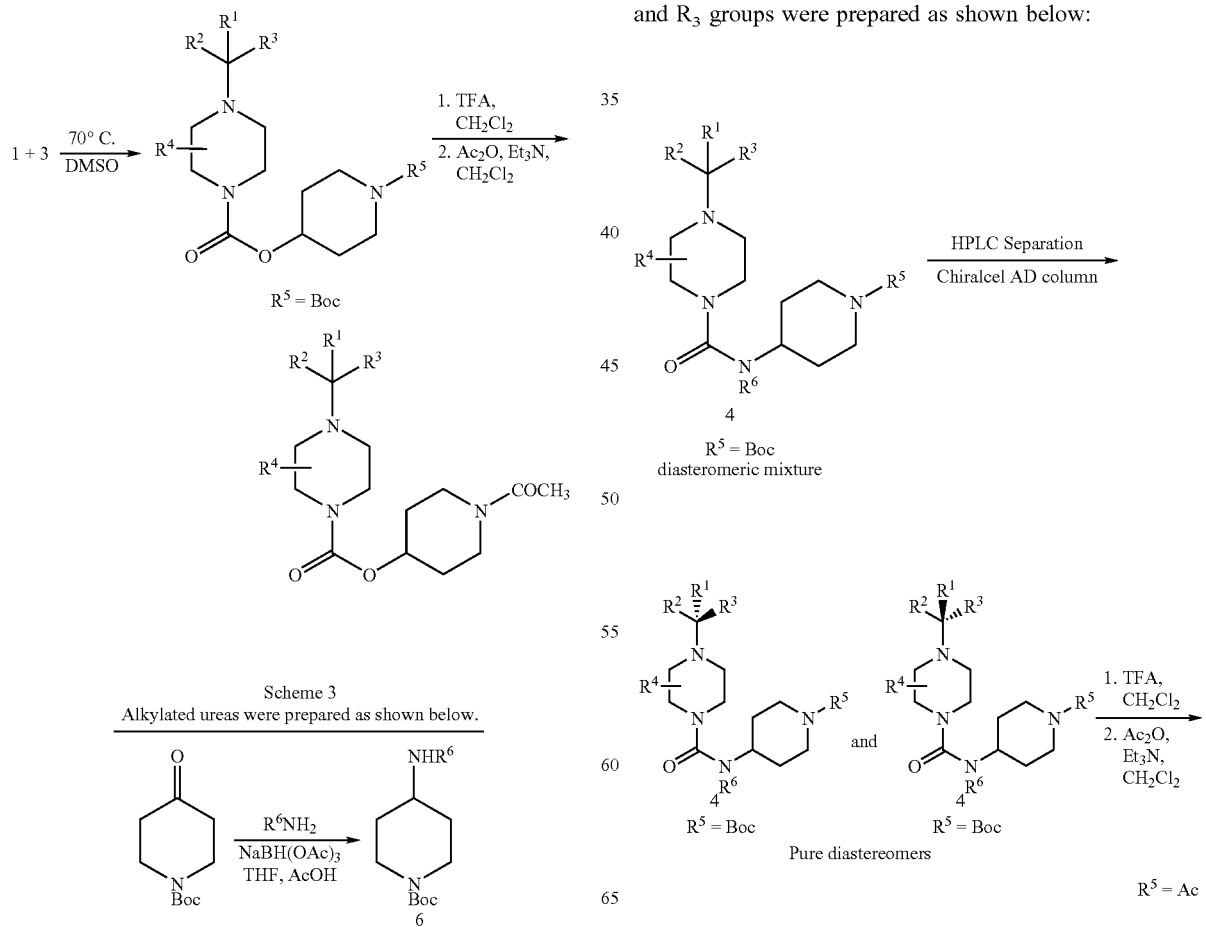
Diastereomerically pure compounds with different $R_1$, $R_2$ and $R_3$ groups were prepared as shown below:
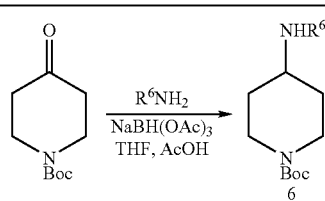

Preparative Example 1

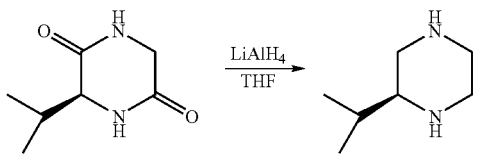

LiAlH$_4$ (1.0 M in THF, 300 mL, 300 mmol) was added slowly to a stirred mixture of (S)-3-isopropyl-2,5-piperazinedione (11.0 g, 70 mmol) in THF (200 mL) at 0° C. under N$_2$. The mixture was stirred and refluxed for 18 hr, cooled to 0° C., and H$_2$O (2×11.0 mL) and 15% NaOH (11.0 mL) were added. EtOAc (300 mL) was added, the mixture was filtered through Celite, and the filter cake was washed with EtOAc (4×100 mL). The solvent was evaporated, the residue was dissolved in EtOAc (200 mL), dried over Na$_2$SO$_4$, and filtered. Evaporation of the solvent gave 7.73 g (86%) of a solid. Crude (S)-2-isopropylpiperazine was used directly without purification. LCMS: MH$^+$=129.

Preparative Example 2

(S)-2-tert-butylpiperazine was prepared by essentially the same procedure given in Preparative Example 1. Oil. LCMS: MH$^+$=143.

Preparative Example 3

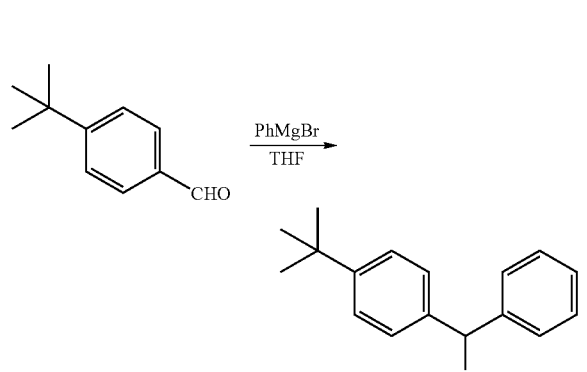

PhMgBr (1.0 M in THF, 22.0 mL, 22 mmol) was added under N$_2$ at 0° C. to a stirred solution of 4-t-butylbenzaldehyde (3.24 g, 20 mmol) in dry THF (20 mL). The mixture was stirred at 0° C. for 10 min, then at 25° C. for 20 hr, poured into saturated aqueous NH$_4$Cl (300 mL), and extracted with CH$_2$Cl$_2$ (3×100 mL). The combined extracts were dried over Na$_2$SO$_4$, filtered, and the solvent was evaporated. Chromatography (silica gel/CH$_2$Cl$_2$) yielded 3.80 g (79%) of a solid.

Preparative Example 4 and 5

By essentially the same procedure set forth in Preparative Example 3, 4-trifluoromethoxybenzhydrol (Preparative Example 4) and 4-trifluoromethylbenzhydrol (Preparative Example 5) were prepared.

Preparative Example 6

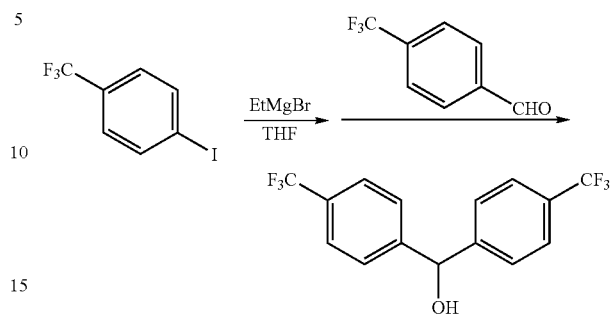

EtMgBr (1.0 M in THF, 75 mL, 75 mmol) was added under N$_2$ to a solution of 4-iodobenzotrifluoride (13.6 g, 50 mmol) in dry THF (50 mL). The solution was stirred at 25° C. for 1 h, then 4-trifluoromethylbenzaldehyde (8.70 g, 50 mmol) was added, the mixture was stirred at 25° C. for 17 hr, and poured into saturated aqueous NH$_4$Cl (300 mL). The mixture was extracted with CH$_2$Cl$_2$ (5×100 mL), the organic extracts were dried over Na$_2$SO$_4$, filtered, and the solvent was evaporated. Chromatography on silica gel with CH$_2$Cl$_2$ gave 8.72 g (55%) of a solid.

Preparative Example 7

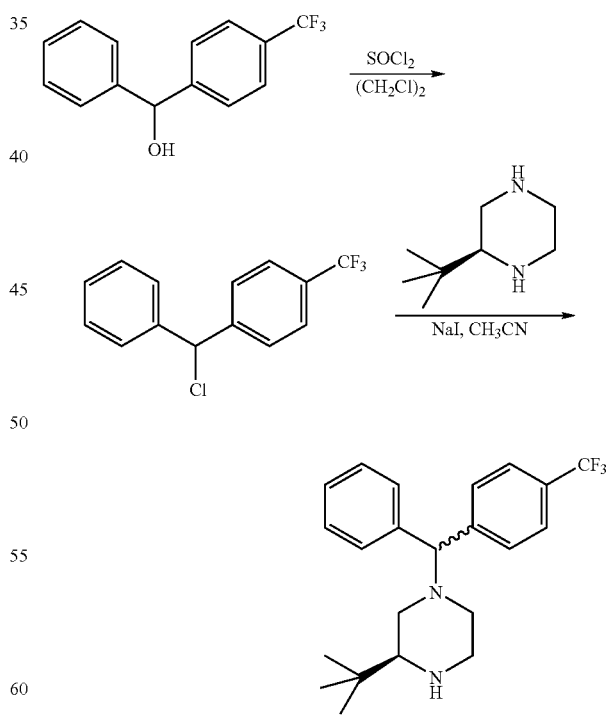

SOCl$_2$ (1.0 mL) was added to a solution of 4-trifluoromethylbenzhydrol (Preparative Example 5, 680 mg, 2.7 mmol) in dry 1,2-dichloroethane (10 mL) and the mixture was refluxed under N$_2$ for 3 hr. The solvent and residual SOCl₂ were evaporated and the resulting oil was dissolved in dry CH₃CN (5 mL) and added to a mixture of (S)-2-t-butylpiperazine (300 mg, 2.11 mmol) and NaI (60 mg, 0.4 mmol). The reaction mixture was stirred and refluxed under N₂ for 24 hr, then poured into 10% aqueous Na₂CO₃ (50 mL) and extracted with CH₂Cl₂ (3×10 mL). The combined extracts were dried over Na₂SO₄, filtered, and the solvent was evaporated. The residue was purified by flash chromatography using 3% MeOH (10% NH₄OH) in CH₂Cl₂ to give 410 mg (52%) of a wax.

Preparative Example 8–12

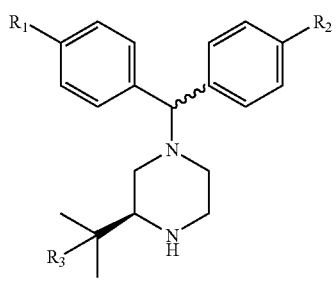

By essentially the same procedure set forth in Preparative Example 7, compounds given in Table 3 were prepared, wherein R₁, R₂ and R₃ are defined.

TABLE 3

| Prep. Example | R₁ | R₂ | R₃ |
|---|---|---|---|
| 8 | H | H | H |
| 9 | H | Cl | H |
| 10 | CF₃ | CF₃ | CH₃ |
| 11 | H | OCF₃ | CH₃ |
| 12 | H | C(CH₃)₃ | CH₃ |

Preparative Example 13

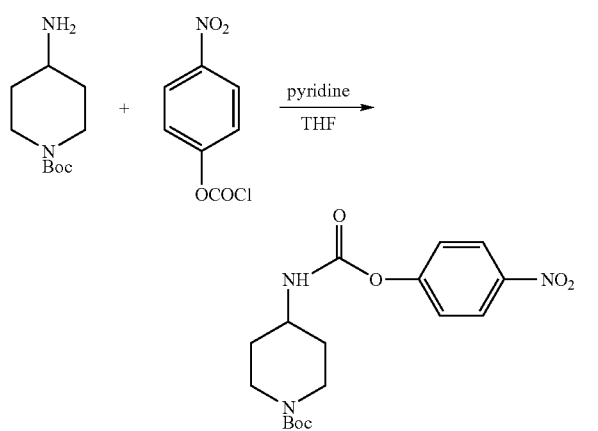

Solution of 4-nitrophenyl chloroformate (4.84 g, 24 mmol) in 20 mL of dry THF was added under N₂ at 0° C. to a stirred solution of N-Boc-4-aminopiperidine (4.00g, 20 mmol) and pyridine (2.20 g, 28 mmol) in 40 mL of dry THF. The mixture was stirred 10 min at 0° C., then at 25° C. for 2 hr. EtOAc (300 mL) was added and the mixture was washed with saturated aqueous NaHCO₃ (5×80 mL). The organic layer was dried over Na₂SO₄, filtered, and the solvent was evaporated. The residue was suspended in 1:1 hexane/ether (200 mL) and filtered. Recrystallization from EtOAc (30 mL) afforded 1.48 g (20%) of a solid. LCMS: MH⁺(—C₄H₉)=310. Mp=162–164° C.

Preparative Example 14

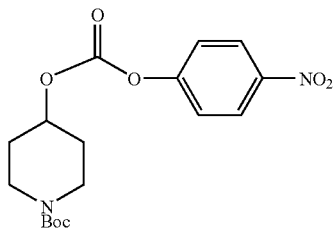

This compound was prepared by essentially the same procedure as given for Preparative Example 13. Solid. LCMS: MH⁺(—C₄H₉)=311. Mp=109–111° C.

Preparative Example 15

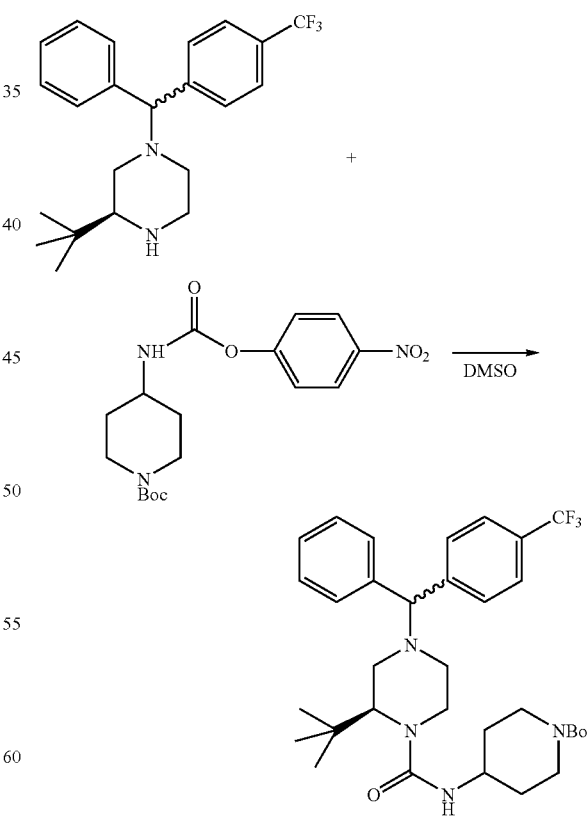

The product from Preparative Example (410 mg, 1.09 mmol) and the product from Preparative Example (440 mg, 1.20 mmol) were dissolved in dry DMSO and the solution was stirred under $N_2$ at 70° C. for 20 hrs. The solution was cooled to rt, ether (100 mL) was added, the solution was washed with 10% NaOH (3×50 mL), dried over $Na_2SO_4$, and filtered. The solvent was evaporated and the residue was chromatographed on silica gel with 2.5% MeOH (10% $NH_4OH$) in $CH_2Cl_2$. 606 mg (92%) of a solid was obtained. LCMS: $MH^+$=603.

Preparative Example 16–21

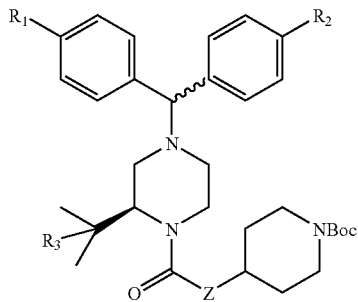

By essentially the same procedure set forth in Preparative Example 15, compounds given in Table 4 were prepared, wherein $R_1$, $R_2$, $R_3$ and Z are defined.

TABLE 4

| Prep. Example | $R_1$ | $R_2$ | $R_3$ | Z |
|---|---|---|---|---|
| 16 | H | H | H | NH |
| 17 | H | Cl | H | NH |
| 18 | H | $OCF_3$ | $CH_3$ | NH |
| 19 | H | $C(CH_3)_3$ | $CH_3$ | NH |
| 20 | $CF_3$ | $CF_3$ | $CH_3$ | NH |
| 21 | $CF_3$ | $CF_3$ | $CH_3$ | O |

Preparative Example 22

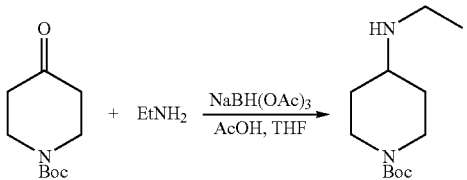

Solution of ethylamine (2.0 M in THF, 20.0 mL, 20.0 mmol) was to N-Boc-4-piperidone (3.00 g, 15.0 mmol). Acetic acid (2. 0 mL) was added, the mixture was stirred for 5 min, then $NaBH(OAc)_3$ (4.22 g, 20.0 mmol) was added. The mixture was stirred under $N_2$ for 24 hr, poured into 10% aqueous $Na_2CO_3$ (300 mL), and extracted with $CH_2Cl_2$ (3×50 mL). The combined extracts were dried over $Na_2SO_4$, filtered, and the solvent was evaporated. The resulting oil (3.20 g, 94%) was used without purification. LCMS: $MH^+$=229.

Preparative Example 23

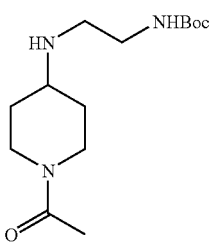

This compound was prepared by essentially the same procedure as given for Preparative Example 22. Oil. LCMS: $MH^+$=286.

Preparative Example 24

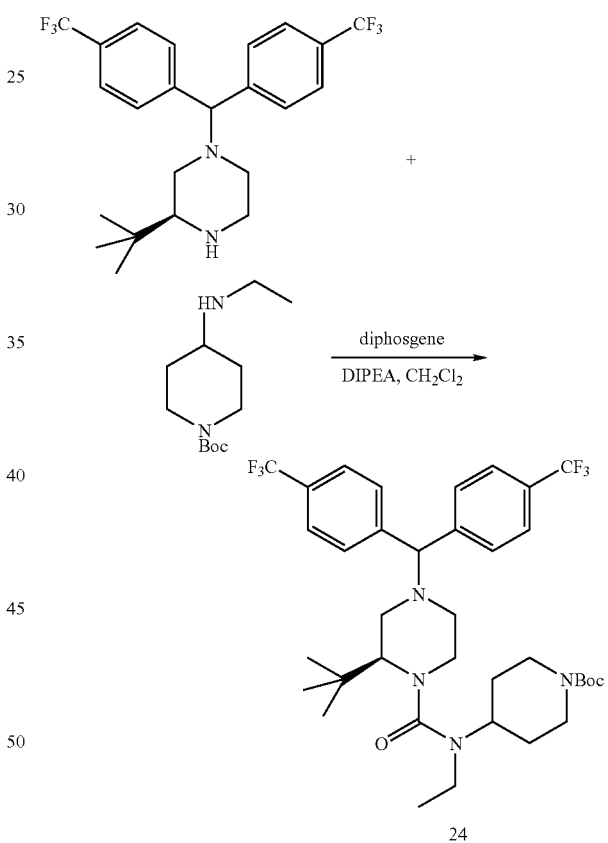

Solution of the product from Preparative Example 22 (200 mg, 0.45 mmol) in dry $CH_2Cl_2$ (2 mL) was added to triphosgene (45 mg, 0.15 mmol) under $N_2$. The mixture was stirred for 1 hr, then solution of the product from Preparative Example (114 mg, 0.50 mmol) and diisopropylethylamine (0.2 mL) in dry $CH_2Cl_2$ (1 mL) was added and stirring was continued for 7 days. The mixture was poured into 10% aqueous $Na_2CO_3$ (50 mL) and extracted with (5×10 mL). The combined extracts were dried over $Na_2SO_4$, filtered, and the solvent was evaporated. The residue was purified by flash chromatography using 4:1 $CH_2Cl_2$/EtOAc to give 35 mg (12%) of a wax. LCMS: $MH^+$=699.

Preparative Examples 25 and 26

By essentially the same procedure set forth in Preparative Example 24, compounds given below were prepared.

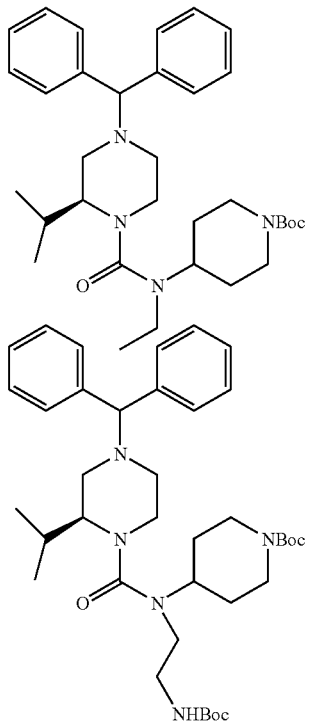

Prep. Examples 25   Prep. Example 26

Pale yellow wax. LCMS: MH$^+$=549.

Preparative Examples 27 and 28

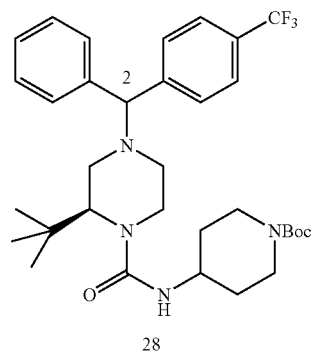

The above compounds were prepared through the separation of diastereomers of the product from Preparative Example by preparative HPLC with a CHIRALPAK AD column using 90:10 hexanes: 2-propanol with 0.2% of diethylamine as eluent.

Preparative Example 27: first eluting isomer (isomer 1). Solid. LCMS: MH$^+$=603. Mp=101–103° C.

Preparative Examples 28: second eluting isomer (isomer 2). Solid. LCMS: MH$^+$=603. Mp=114–116° C.

Preparative Example 29 and 30

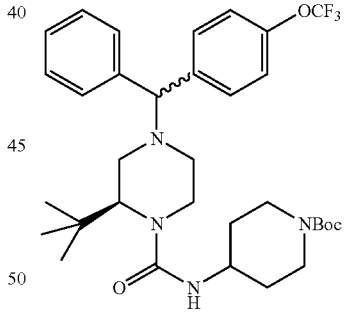

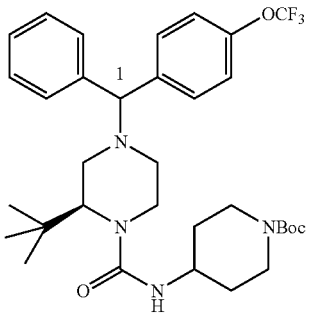

-continued

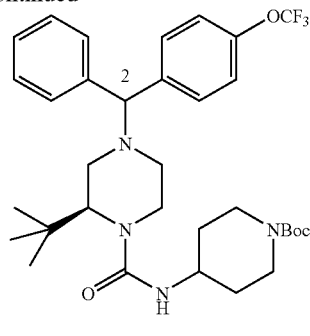

The separation was similar as for Preparative Example 27 and 28.
Preparative Example 29: first eluting isomer (isomer 1).
Preparative Example 30: second eluting isomer (isomer 2).

Preparative Examples 31 and 32

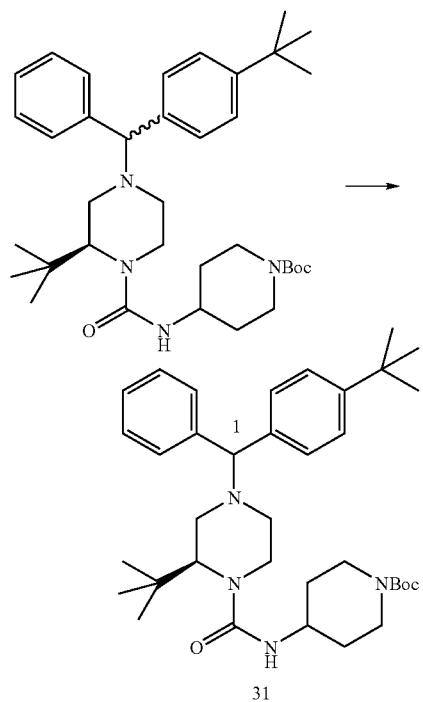

The separation was similar as for Preparative Example 27 and 28.
Preparative Example 31: first eluting isomer (isomer 1).
Preparative Example 32: second eluting isomer (isomer 2).

Example 1

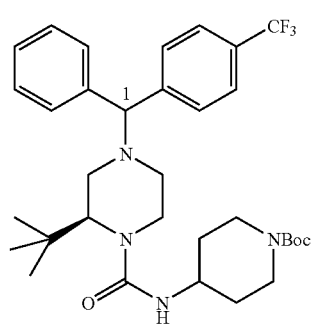

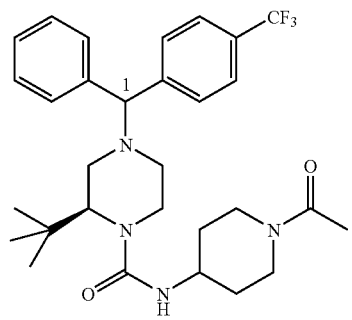

TFA (0.3 mL) was added to a solution of SM (200 mg, 0.33 mmol) in anhydrous $CH_2Cl_2$ (3 mL) at 0° C. under $N_2$. The mixture was stirred at 0° C. for 15 min, then 1.0 mL of TFA was added and the stirring was continued for another 50 min at 0° C. The mixture was poured onto solid $K_2CO_3$ (5 g), $H_2O$ (50 mL) was added, and the mixture was extracted with $CH_2Cl_2$ (4×10 mL). The extracts were dried over $MgSO_4$, filtered, and the solvent was evaporated. The residue was dissolved in anhydrous $CH_2Cl_2$ (4 mL), and $Ac_2O$ (0.20 mL) and TEA (0.40 mL) were added. The mixture was stirred under $N_2$ for 24 hrs, poured into 10% aqueous $Na_2CO_3$ (30 mL), and extracted with $CH_2Cl_2$ (3×10 mL). The combined extracts were dried over $Na_2SO_4$, filtered, and the solvent was evaporated. The residue was purified by flash chromatography using 3% MeOH (10% $NH_4OH$) in $CH_2Cl_2$ to give 130 mg (72%) of a solid. LCMS: $MH^+$=545. Mp=119–121° C.

Examples 2–15

By essentially the same procedure set forth in Example 1, compounds given in Table 5 were prepared.

TABLE 5

| Prep. Example | Compound | Data |
| --- | --- | --- |
| 2 | | LCMS: MH⁺ = 463<br>Mp = 102–104° C. |
| 3 | ca 1:1 mixture of diastereomers | LCMS: MH⁺ = 497<br>Mp = 103–106° C. |
| 4 | ca 1:1 mixture of diastereomers | LCMS: MH⁺ = 545<br>Mp = 94–98° C. |
| 5 | | LCMS: MH⁺ = 613<br>Mp = 132–135° C. |

TABLE 5-continued

| Prep. Example | Compound | Data |
|---|---|---|
| 6 | | LCMS: MH⁺ = 614<br>Mp = 78–81° C. |
| 7 | | LCMS: MH⁺ = 491<br>Mp = 58–61° C. |
| 8 | | LCMS: MH⁺ = 641<br>Mp = 85–88° C. |
| 9 | ca 1:1 mixture of diastereomers | LCMS: MH⁺ = 561<br>Mp = 100–107° C. |

TABLE 5-continued

| Prep. Example | Compound | Data |
|---|---|---|
| 10 | (structure: 4-tert-butylphenyl/phenyl methyl on piperazine with t-Bu, urea to 1-acetylpiperidin-4-yl) ca 1:1 mixture of diastereomers | LCMS: MH⁺ = 533<br>Mp = 128–134° C. |
| 11 | (structure: 4-CF₃-phenyl/phenyl methyl on piperazine with t-Bu, urea to 1-acetylpiperidin-4-yl) isomer 2 | LCMS: MH⁺ = 545<br>Mp = 124–127° C. |
| 12 | (structure: 4-OCF₃-phenyl/phenyl methyl on piperazine with t-Bu, urea to 1-acetylpiperidin-4-yl) isomer 1 | LCMS: MH⁺ = 561<br>Mp = 106–109° C. |
| 13 | (structure: 4-OCF₃-phenyl/phenyl methyl on piperazine with t-Bu, urea to 1-acetylpiperidin-4-yl) isomer 2 | LCMS: MH⁺ = 561<br>Mp = 102–105° C. |

TABLE 5-continued

| Prep. Example | Compound | Data |
|---|---|---|
| 14 | (isomer 1) | LCMS: MH⁺ = 533<br>Mp = 128–130° C. |
| 15 | (isomer 2) | LCMS: MH⁺ = 533<br>Mp = 129–131° C. |

Example 16

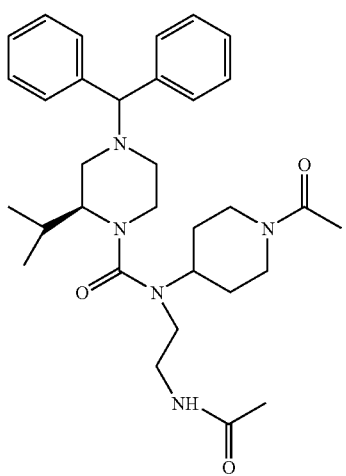

This compound was prepared from the corresponding precursor (Preparative Example 26) by essentially same method as given for Example 1. CMS: MH⁺=548. Mp=90–92° C.

The compounds of the invention can be useful as inhibitors of type 3 17β-hydroxysteroid dehydrogenase. This utility was demonstrated by the following assay.

BIOLOGICAL DATA

17β-hydroxysteroid Dehydrogenase Inhibition Data Methods:

To prepare human recombinant type 3 17β-hydroxysteroid dehydrogenase enzyme, HEK-293 cells stably transfected with human 17β-HSD type 3 were cultured to confluency and harvested for enzyme. The cells were suspended in isolation buffer (20 mM $KH_2PO_4$, 1 mM EDTA, 0.25 M Sucrose, 1 mM PMSF, 5 μg/ml pepstatin A, 5 μg/ml antipain and 5 μg/ml leupeptin) to a concentration between $5.0 \times 10^6$ and $1.0 \times 10^7$ cells/ml. The cells were sonicated on ice using a micro-ultrasonic cell disrupter at an output setting of No.40 for four 10 second bursts. The broken cells were then centrifuged at 100,000×g for 60 min at 4° C., and the resulting pellet was resuspended, aliquoted into microfuge tubes, and stored at −80° C.

To measure conversion of $^{14}C$-androstenedione to $^{14}C$-testosterone, reaction buffer (12.5 mM $KH_2PO_4$, 1 mM EDTA), NADPH cofactor (1 mM final), test compound, 17β-HSD3 enzyme (30 μg protein) and $^{14}C$-androstenedione substrate (100 nM; 2.7 nCi/tube) were added to 13×100 borosilicate glass tubes to a total volume of 0.5 mL/tube. The tubes were placed in a prewarmed 37° C. water bath for 30 minutes. The reaction was then stopped by adding 1 ml of ethyl ether. The tubes were centrifuged for 20 minutes at 3000 rpm at 4° C. in a table top centrifuge and then snap frozen in a dry ice-methanol bath. The ether layer was decanted into another glass tube, and then evaporated to dryness using compressed nitrogen gas. The samples were resuspended in chloroform (20 mL) and spotted onto silica G60 thin layer chromatography plates. $^{14}$C-Androstenedione substrate and $^{14}$C-testosterone product were separated by placing the plates in chloroform:ethyl acetate (3:1). The plates were dried, exposed overnight, scanned and quantitated on a FUJI FLA2000 phosphorimager.

Compounds of this invention exhibited a range of 17B-Hydroxysteroid dehydrogenase Type 3 binding activity from about 0.005 nM to about >100 nM. Several compounds of this invention have a binding activity in the range of about 0.005 nM to 10 nM.

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound represented by the structural formula:

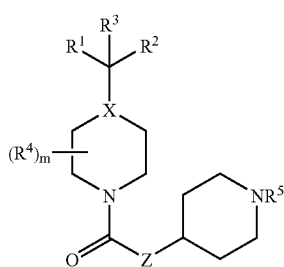

Formula I wherein:
X is N;
Z is O or N(R$^6$);
R$^1$ and R$^2$ are the same or different, each being independently selected from the group consisting of aryl, and aralkyl, wherein each of said aryl, and aralkyl can be unsubstituted or optionally independently substituted with one or more moieties which can be the same or different, each moiety being independently selected from the group consisting of halogen, alkyl, aryl, aralkyl, cycloalkyl, CF$_3$, CN, —OCF$_3$, —OR$^6$, —C(O)R$^7$, —NR$^6$R$^7$, —C(O)OR$^6$, —C(O)NR$^6$R$^7$, —SR$^6$, —S(O$_2$)R$^7$, —S(O$_2$)NR$^6$R$^7$, —N(R$^6$)S(O$_2$)R$^7$, —N(R$^6$)C(O)R$^7$ and —N(R$^6$)C(O)NR$^6$R$^7$;
R$^3$ is H or —OR$^6$, with the proviso that when X is N, R$^3$ is not —OR$^6$;
R$^4$ is selected from the group consisting of H, alkyl, aryl, cycloalkyl, aralkyl, and aralkyl;
m is a number from 0 to 4, and when m is more than 1, the R$^4$ groups can be the same or different and are independently selected;
R$^5$ is —C(O)R$^7$ or —S(O$_2$)R$^7$;
R$^6$ is selected from the group consisting of H, alkyl, aryl, aralkyl, and cycloalkyl, wherein each of said alkyl, aryl, aralkyl, and cycloalkyl can be unsubstituted or optionally independently substituted with one or more moieties which can be the same or different, each moiety being independently selected from the group consisting of halogen, alkyl, aryl, cycloalkyl, CF$_3$, OCF$_3$, CN, —OR$^7$, —NHR$^7$, —N(R$^7$)$_2$, —CH$_2$OR$^7$, —C(O)R$^7$, —C(O)OR$^7$, —C(O)NHR$^7$, —C(O)N(R$^7$)$_2$, —SR$^7$, —S(O$_2$)R$^7$, —S(O$_2$)NHR$^7$, —S(O$_2$)N(R$^7$)$_2$, —N(R$^7$)S(O$_2$)R$^7$, —N(R$^7$)C(O)R$^7$, —N(R$^7$)C(O)NHR$^7$ and —N(R$^7$)C(O)N(R$^7$)$_2$; and R$^7$ is selected from the group consisting of alkyl, aryl, aralkyl, —OR$^6$, —NHR$^6$, and —N(R$^6$)$_2$, wherein each of said alkyl, aryl, and aralkyl can be unsubstituted or optionally substituted with one or more moieties which can be the same or different, each moiety being independently selected from the group consisting of halogen, alkyl, aryl, cycloalkyl, CF$_3$, OCF$_3$, CN, —OR$^6$, —NHR$^6$, —N(R$^6$)$_2$, —CH$_2$OR$^6$, —C(O)OR$^6$, —C(O)NHR$^6$, —C(O)N(R$^6$)$_2$, —SR$^6$, —S(O$_2$)R$^6$, —S(O$_2$)NHR$^6$, —S(O$_2$)N(R$^6$)$_2$, —N(R$^6$)S(O$_2$)R$^6$, —N(R$^6$)C(O)R$^6$, —N(R$^7$)C(O)NHR$^6$ and —N(R$^7$)C(O)N(R$^7$)$_2$, further wherein the two R$^6$ or the two R$^7$ groups in the moieties —N(R$^6$)$_2$ and —N(R$^7$)$_2$ respectively can be the same or different and are independently selected, and still further wherein any two adjacent alkyl substituents on an aryl can be joined together to form a methylenedioxy or ethylenedioxygroup.

2. The compound of claim 1, wherein Z is O.

3. The compound of claim 1, wherein Z is N(R$^6$).

4. The compound of claim 1, wherein R$^1$ and R$^2$ are the same and are aryl, wherein said aryl is either unsubstituted or optionally independently substituted with one or more moieties which can be the same or different, each moiety being independently selected from the group consisting of halogen, alkyl, —CF$_3$, —CN, —OCF$_3$, —OR$^6$, —C(O)R$^7$, and —C(O)OR$^6$.

5. The compound of claim 1, wherein R$^3$ is H.

6. The compound of claim 1, wherein R$^4$ is H.

7. The compound of claim 1, wherein R$^5$ is —C(O)R$^7$ or —S(O$_2$)R$^7$.

8. The compound of claim 7, wherein R5 is —C(O)R$^7$.

9. The compound of claim 1, wherein R$^6$ is selected from the group consisting of H, alkyl, aryl, —CF$_3$, —C(O)R$^7$ and —S(O$_2$)R$^7$.

10. The compound of claim 9, wherein R$^6$ is H, methyl or CF$_3$.

11. The compound of claim 1, wherein R$^7$ is selected from the group consisting of alkyl, aralkyl and aryl.

12. The compound of claim 3, wherein R$^6$ is H.

13. The compound of claim 4, wherein R$^1$ and R$^2$ are the same and are phenyl, wherein said both phenyl groups are unsubstituted.

14. The compound of claim 4, wherein R$^1$ is unsubstituted phenyl and R$^2$ is a phenyl substituted with one or more moieties selected from the group consisting of halogen, alkyl, —CF$_3$, —OCF$_3$, and —C(O)R$^7$.

15. The compound of claim 11, wherein R$^7$ is alkyl.

16. A compound of the formula:

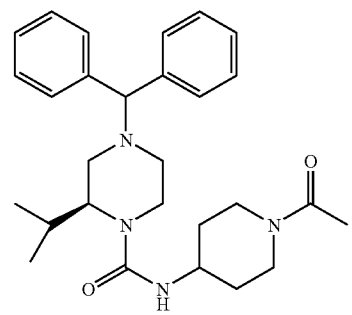

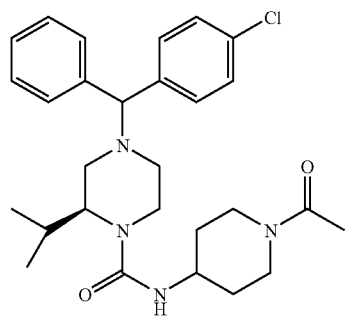
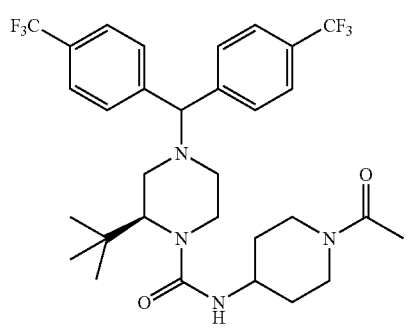
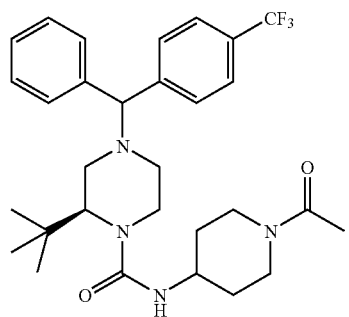
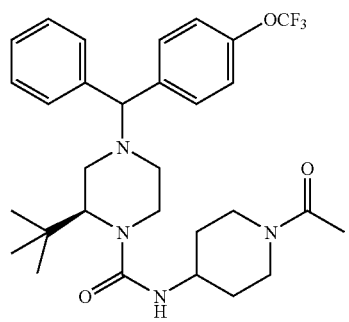
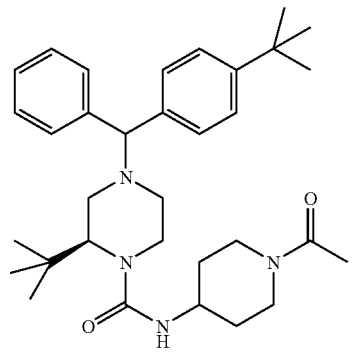
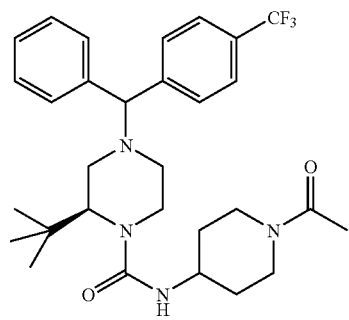
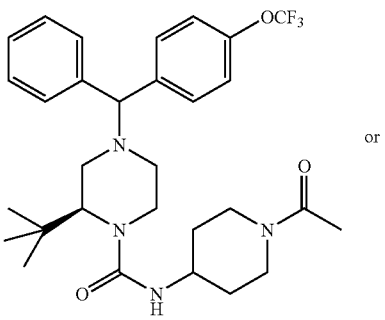
or
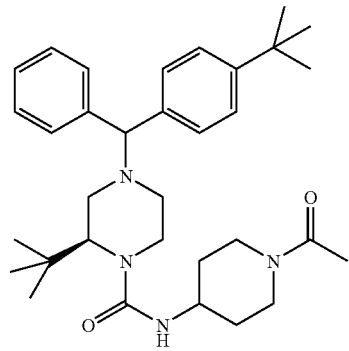
or stereoisomer thereof, or a pharmaceutically acceptable salt or solvate of said compound or of said stereoisomer.

17. A compound having the structure:

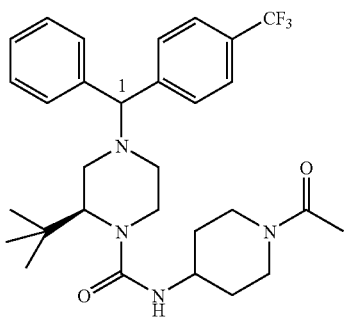

or a pharmaceutically acceptable salt or solvate thereof.

18. A compound having the structure:

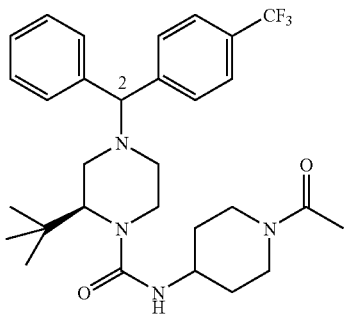

or a pharmaceutically acceptable salt or solvate thereof.

19. A compound having the structure:

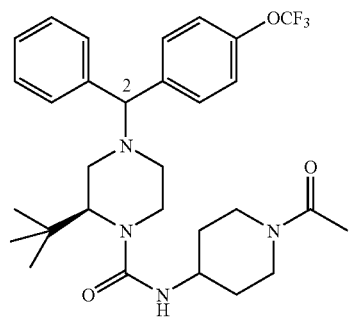

or a pharmaceutically acceptable salt or solvate thereof.

20. A compound having the structure:

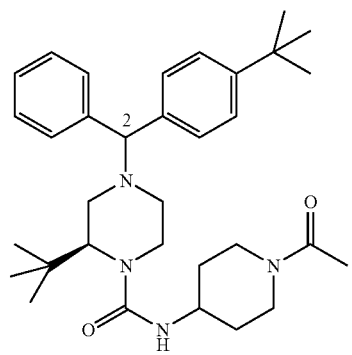

or a pharmaceutically acceptable salt or solvate thereof.

21. A pharmaceutical composition comprising a therapeutically effective amount of at least one compound of claim 1 in combination with at least one pharmaceutically acceptable carrier.

* * * * *